(12) United States Patent
Webb et al.

(10) Patent No.: US 6,534,686 B1
(45) Date of Patent: Mar. 18, 2003

(54) METHOD FOR PRODUCING BISPHENOL CATALYSTS AND BISPHENOLS

(75) Inventors: Jimmy Lynn Webb, Ballston Lake, NY (US); James Lawrence Spivack, Cobleskill, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/954,914

(22) Filed: Sep. 18, 2001

(51) Int. Cl.⁷ ............................................. C07C 39/16
(52) U.S. Cl. ...................................... 568/728; 568/727
(58) Field of Search .................................. 568/727, 728

(56) References Cited

U.S. PATENT DOCUMENTS 5,414,151 A    5/1995  Pressman et al.
5,428,075 A    6/1995  Pressman et al.

FOREIGN PATENT DOCUMENTS

| JP | 57-85335  | * | 5/1982 |
| JP | 11-179210 |   | 7/1999 |
| JP | 11-246458 |   | 9/1999 |

\* cited by examiner

*Primary Examiner*—Michael L. Shippen
(74) *Attorney, Agent, or Firm*—Andrew J. Caruso; Noreen C. Johnson

(57) ABSTRACT

This disclosure relates to a method for producing and using catalysts in the production of bisphenols, and in particular to a method for producing catalysts which contain attached mercaptan promoters, and using these catalysts in the production of bisphenol-A and its derivatives.

16 Claims, No Drawings

METHOD FOR PRODUCING BISPHENOL CATALYSTS AND BISPHENOLS

BACKGROUND OF THE INVENTION

This disclosure relates to a method for producing and using catalysts for the production of bisphenols, and in particular to a method for producing catalysts which contain attached mercaptan promoters, and using these catalysts in the production of bisphenol-A, and its derivatives.

Typical bisphenols, such as 4,4'-isopropylidenediphenol, e.g., bisphenol-A (BPA), are widely employed as monomers in the manufacture of polymeric materials, such as engineering thermoplastics. For example, BPA is a principal monomer used in the manufacture of polycarbonate. Bisphenols are generally prepared by the electrophilic addition of aldehydes, or ketones such as acetone, to aromatic hydroxy compounds such as phenol, in the presence of an acidic catalyst composition. These types of reactions are also referred to as acid catalyzed condensation reactions. Commercially, sulfonated polystyrene resin cross-linked with divinylbenzene, e.g., PS-DVB, is typically used as a solid acid component of the catalyst composition. Reaction promoters can also be employed as part of a catalyst composition to improve the reaction rate, and selectivity, of the desired condensation reaction; in the case of BPA, the desired selectivity is for the para-para isomer. Promoters can be present as unattached molecules in the bulk reaction matrix, e.g., "bulk-promoters", or can be attached to the resin through ionic linkages, e.g., "attached-promoters". A useful class of promoter is the mercaptans, specifically thiols, e.g., organosulfur compounds which are derivatives of hydrogen sulfide. Unfortunately, due to the reactivity of the S—H sulfhydryl functionality, thiol promoters are prone to deactivation during their synthesis and under typical conditions used to attach the promoter to the resin, because they readily oxidize at the sulfur atom to inactive disulfide compounds, with —S—S— linkages, that do not function as promoters in the catalytic production of bisphenols. Consequently, a long felt yet unsatisfied need exists for a new and improved method to attach mercaptan promoters to catalyst supports to produce highly active and selective catalysts for the production of bisphenols.

SUMMARY OF THE INVENTION

In one embodiment, the present disclosure is drawn to method for producing a catalyst composition which catalyzes the formation of bisphenols from aromatic hydroxy compounds and carbonyl containing compounds, said method comprising the step of attaching a sulfur-protected mercaptan promoter component to a solid acid support component comprising a protic acid functionality, said sulfur-protected mercaptan promoter component having the following structure (I),

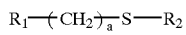
(I)

wherein $R_1$ is a functionality selected from the group consisting of a positively charged ammonium functionality, a positively charged guanidinium functionality, a positively charged phosphonium functionality, and a neutral amine;
wherein a is between about 0 and about 11; and
wherein $R_2$ is a sulfur protecting functionality which is one member selected from the group consisting of a tertiary alkyl functionality, an ester functionality, a carbonate functionality, and a benzyl functionality which is attached to the sulfur atom via the benzylic methylene carbon.

In another embodiment, the present disclosure is drawn to a method for forming bisphenols, comprising the step of reacting an aromatic hydroxy compound with a carbonyl compound in the presence of a catalyst composition, said catalyst composition comprising a solid acid component and a sulfur-protected mercaptan promoter component having the following structure (I),

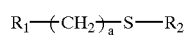

wherein $R_1$ is a functionality selected from the group consisting of a positively charged ammonium functionality, a positively charged guanidinium functionality, a positively charged phosphonium functionality, and a neutral amine;
wherein a is between about 0 and about 11; and
wherein $R_2$ is a sulfur protecting functionality which is one member selected from the group consisting of a tertiary alkyl functionality, an ester functionality, a carbonate functionality, and a benzyl functionality which is attached to the sulfur atom via the benzylic methylene carbon.

DETAILED DESCRIPTION

The present disclosure is directed to a method for producing and using catalysts for the production of bisphenols, and is suitable for the preparation of attached-promoter catalysts, which can effectively catalyze the formation of bisphenols from aromatic hydroxy compounds and carbonyl containing compounds. In the context of the present disclosure, the term "catalyst" refers to a composition, wherein the individual constituents of the composition are referred to as "components". In the context of the present disclosure, a typical catalyst comprises a "support" component that is generally a polymeric material, also referred to as a "resin", comprising a protic acid functionality, and a "promoter" component that is generally an organic compound. As used herein, the term "functionality" is defined as an atom, or group of atoms acting as a unit, whose presence imparts characteristic properties to the molecule to which the functionality is attached. In the context of the present disclosure, a "protic acid functionality" is defined as a group of atoms that are covalently attached to the polymeric support component of the catalyst, which can act as a source of protons, e.g., a Brönsted acid, and upon deprotonation the counter-anion can serve as an anionic moiety of an ionic bond with a cationically charged promoter component. A suitable example of a support component is a polystyrene resin, cross-linked with divinylbenzene. Suitable examples of protic acid functionalities, which are attached to the support component, are a sulfonic acid functionality, which upon deprotonation produces a sulfonate anion functionality, a phosphonic acid functionality, which upon deprotonation produces a phosphonate anion functionality, and a carboxylic acid functionality, which upon deprotonation produces a carboxylate anion functionality. For example, in one embodiment of the present disclosure, the support component is a polystyrene resin, cross-linked with 4% of divinylbenzene, and functionalized with sulfonic acid groups.

Attached-promoter components are typically organic compounds, which can readily form stable cationic species. Suitable examples of promoters include, but are not limited to, alkylammonium mercaptans, alkylguanidinium mercaptans, alkylphosphonium mercaptans, and aminomercaptans. As used herein, the term "mercaptan" is defined as an organosulfur compound, which is a derivative of hydrogen sulfide, and the term "aminomercaptan" is defined as an organosulfur compound, which further comprises a nitrogen functionality. Suitable examples of aminomercaptans include, pyridyl mercaptans, benzimidazole mercaptans, phthalimido mercaptans, benzothiazole mercaptans, and imidazole mercaptans. In the case of aminomercaptans that comprise ring systems, a sulfur containing chain can be bonded to the ring system at any one of ring location that is capable of bonding a substituent. For example, in the case of aminopyridine mercaptans, a sulfur containing functionality can be appended to pyridine ring at the 2, 3, or 4 ring position. Furthermore, in each of the classes of mercaptan promoter listed above, i.e. alkylammonium mercaptans, alkylguanidinium mercaptans, alkylphosphonium mercaptans, and aminomercaptans, more than one sulfur containing chains per amino group can be present in the promoter. For example, in the case of pyridyl mercaptans, the pyridine ring can be substituted with up to 5 sulfur-containing chains. Substituent groups, which are typically represented by the symbol R in chemical structures, can also be attached to a promoter to adjust the promoter's electronic properties, steric properties, and combinations thereof, to affect the reactivity of the overall catalyst composition. Suitable promoter substituent groups include, but are not limited to, a hydrogen, a fluoride, a bromide, a chloride, an iodide, a vinyl group, a hydroxide, an alkoxide functionality comprising between about 1 and about 11 carbon atoms, an aryloxide functionality comprising at least about 6 carbon atoms, an aliphatic functionality comprising between about 1 and about 11 carbon atoms, and an aromatic functionality comprising at least about 6 carbon atoms. In the case of aminomercaptans that comprise ring systems, a substituent group can also be a cycloaliphatic ring comprising at least about 5 carbon atoms, said cycloaliphatic ring being fused to the amino ring through an adjacent ring substituent, or a cycloaromatic ring comprising at least about 6 carbon atoms, said cycloaromatic ring being fused to the amino ring through an adjacent ring substituent.

Attachment of the amino based mercaptan promoter to the polymeric support is typically made via an ionic linkage between a cationically charged promoter, which in the case of an aminomercaptan results from the protonation at the nitrogen atom, and the anionically charged deprotonated acid functionality on the resin backbone. The attachment of an aminomercaptan promoter to an acid functionalized polymeric support can be performed in an aqueous solution. Herein, the term "aqueous solution" includes those solutions where water is present as a solvent. For example, a protected mercaptan promoter, such as [2-(2'-ethylthioacetate) pyridine], can be attached to a sulfonic acid functionalized PS-DVB resin through an ionic linkage formed between a [2-(2'-ethylthioacetate)pyridinium]$^+$ cation, and a sulfonate anion on the polymeric support, by mixing the PS-DVB resin and the mercaptan promoter together in water. Alternatively, the aminomercaptan promoter can be attached to an acid functionalized polymeric support in an organic medium comprising an aromatic hydroxy compound, such as phenol.

In one embodiment of the present disclosure, the aminomercaptan promoter is protected at the sulfur atom, before it is attached to the support with a typical protecting group functionality used to protect Group 16 elements, such as oxygen and sulfur, from oxidation. As used herein, the term "protecting group" refers to a functionality which inhibits a specific type of reactivity, and in the context of the present disclosure, the protecting group attached to the sulfur atom of the aminomercaptan promoter is present in order to inhibit the oxidation of sulfur atom; typically, unprotected mercaptan sulfhydryl groups are readily oxidized to disulfides, or more highly oxidized groups, during synthesis or under the conditions in which the promoters are attached to the polymeric supports. In the context of the present disclosure, suitable examples of sulfur protecting groups include, but are not limited to, aliphatic functionalities that form stable carbocations, ester functionalities, carbonate functionalities, and benzylic functionalities. When used in conjunction with the term protecting group, the term "aliphatic" refers to an organic compound composed of hydrogen atoms and carbon atom arranged in a branched chain, capable of forming a stable carbocation species. For example, in one embodiment the aliphatic protecting group is a tertiary butyl group, e.g., —C(CH$_3$)$_3$. However, when used in conjunction with the term "substituent", the term "aliphatic" refers more broadly to an organic compound composed of hydrogen atoms and carbon atoms which contains between about 1 and about 11 carbon atoms, arranged in either a linear or branched chain. Furthermore, when used in conjunction with the term "substituent", the term "aromatic" is defined as an organic compound composed of hydrogen atoms and carbon atoms, which contains at least about 6 cyclic conjugated carbon atoms.

Suitable examples of ester functionalities, e.g., —C(O)R wherein R can be either an aliphatic substituent or an aromatic substituent, include those esters which contain between about 1 and about 11 carbon atoms, such as an acetate group, e.g., —C(O)CH$_3$. Suitable examples of carbonate functionalities, e.g., —C(O)OR, include carbonates with aliphatic substituents or aromatic substituents. An example of a suitable aliphatic carbonate protecting group is as a tert-butoxy carbonate, e.g., —C(O)O—$^t$Bu. An example of a suitable aromatic carbonate protecting group is as a phenyl carbonate group, e.g., —C(O)OPh. Suitable examples of benzylic functionalities, e.g., —CH$_2$(aryl), include those benzylic groups which contain at least 7 carbon atoms, such as a benzyl group, e.g., —CH$_2$(C$_6$H$_5$).

In another embodiment, the present disclosure relates to a method for using the catalysts disclosed herein, to catalyze the formation of bisphenols, such as 4,4'-isopropylidenediphenol. In the context of the present disclosure, the term "catalyze", when used in reference to a catalyst composition, refers to the facilitation of a specific chemical transformation between one or more chemical species, at a reaction rate or selectivity, which is greater than, or equal to, a predetermined reference reaction rate, or reference selectivity, under a specific set of reaction conditions. In the context of the present disclosure, the reaction that is being catalyzed is a condensation reaction between an aromatic hydroxy compound and carbonyl-comprising compound to form a bisphenol, which typically occurs in a liquid reaction mixture. Herein, the term "liquid reaction mixture" is defined as a mixture of compounds, which are present predominantly in a liquid state at ambient room temperature and pressure (e.g., about 25° C. and about 0.1 MPa). Liquid reaction mixtures can be homogeneous liquid mixtures composed of one of more phases (e.g., biphasic liquid reaction mixtures), or heterogeneous liquid-solid mixtures comprising components that are present in the solid state (e.g., precipitates).

The components which are present in a typical liquid reaction mixture of a condensation reaction to produce bisphenols include, but are not limited to, the desired bisphenol, byproducts of the condensation reaction such as water, and bisphenols other than the desired bisphenol, soluble components of the catalyst composition, insoluble components of the catalyst composition, and unreacted starting materials, e.g. an aromatic hydroxy compound, and a carbonyl containing compound. Suitable types of aromatic hydroxy compounds include, but are not limited to, monocyclic aromatic compounds comprising at least one hydroxy group, and polycyclic aromatic compounds comprising at least one hydroxy group. Illustrative examples of suitable aromatic hydroxy compounds include, but are not limited to, phenol, alkylphenols, alkoxyphenols, naphthols, alkylnaphthols, and alkoxynaphthols. As used herein, the term "carbonyl containing" compounds refers to organic compounds which contain an sp$^2$ hybridized carbon which is double bonded to an oxygen atom, and includes aldehydes, and ketones. An example of a suitable aldehyde is acetaldehyde. An example of a suitable ketone is acetone.

The condensation reaction can be influenced by various reaction conditions including, but not limited to, reactor vessel pressure, reaction temperature, agitation rate, the pH of the reaction mixture, catalyst concentration, the weight % of various components of the liquid reaction mixture including, but not limited to, the weight % of an aromatic hydroxy compound, the weight % of a carbonyl containing compound, the weight % of a desired bisphenol, and the weight % of water. For example, typical reaction conditions for the catalytic production of BPA using the catalysts described herein and an incremental flow reactor include, but are not limited to, temperatures between about 55° C. and about 85° C., acetone concentrations of between about 1% and about 10%, and space velocities between about 0.1 pounds of feed per pound of solid catalyst per hour and 10 pounds of feed per pound of solid catalyst per hour.

The following examples are included to provide additional guidance to those skilled in the art in practicing the claimed invention. The examples provided are merely representative of the present disclosure. Accordingly, the following examples are not intended to limit the invention, as defined in the appended claims, in any manner.

Examples in Table 1: For each of the examples 1–3, and the comparative examples C1–C3, listed in Table 1, the following synthetic procedure was used to prepare the catalyst with the promoters listed in Table 1. About 30 mg to about 55 mg of dry Rohm and Haas A131 resin beads (sulfonated polystyrene, crosslinked with about 4% divinylbenzene) with about 4 times it's mass of molten phenol were heated at about 70° C. for about one hour. To this mixture was added a 540 mM phenol solution of the promoter, in an amount sufficient to yield a reaction mixture, which was about 1 mmole of promoter per gram of dry resin. The resulting reaction mixture was stirred for about 4 hours, after which time a portion of the phenol was removed. The resulting mixture of catalyst in phenol had a mass of about 3.5 times the mass of the initial dry resin. To demonstrate the catalytic activity of the catalyst prepared by the procedure described above, a condensation reaction was performed by feeding a solution of about 9 wt % acetone in phenol, while maintaining a reactor temperature of 70deg C. in an incremental flow reactor run at a space velocity of about 2.7 mg feed/mg dry resin/hr and a liquid residence time of about 0.9 hr. After about 40 cycles of alternate feeding and reactor mixture removal, the composition in the reactor was near steady state and samples were taken and analyzed for 4,4'-isopropylidenediphenol (p,p-BPA), and 4,2'-isopropylidenediphenol (o,p-BPA), ) and eight other compounds known to sometimes be formed in smaller amounts. Table 1 summarizes the results by tabulating the wt % p,p-BPA produced, and the ratio of pp-BPA to o,p-BPA ("pp/op ratio") and the overall pp-BPA selectivity, which is defined as the weight % p,p-BPA as a fraction of all products measured.

TABLE 1

| promoter | pp/op | pp selectivity | wt % pp-BPA |
|---|---|---|---|
| C1 2-(2'-mercapto ethyl)-pyridine | 28.3 | 94.7 | 23.1 |
| 1 2-(2'-thioacetate ethyl)-pyridine | 28.8 | 94.7 | 22.0 |
| C2 2-mercaptoethylbenzimidazole | 25.2 | 94.2 | 21.0 |
| 2 N,S-diacetyl-2-mercaptoethyl-benzimidazole | 25.1 | 94.2 | 20.3 |
| C3 N-(2'-mercaptoethyl)-phthalimidine | 17.3 | 92.8 | 19.6 |
| 3 S-acetyl-N-(2'-mercaptoethyl)-phthalimidine | 17.3 | 92.7 | 20.5 |

Examples in Table 2: The experimental procedure for the preparation of the catalysts with the promoters listed in Table 2 was similar to that described above for the examples in Table 1, except that the concentration of the promoter solutions was about 490 mM. Correspondingly, the procedure used for the formation of BPA was similar to that described above, except the space velocity was about 3.0 mg feed/mg dry resin/hr and the liquid residence time was about 1 hr. Results are summarized in Table 2.

TABLE 2

| promoter | pp/op | pp selectivity | wt % pp-BPA |
|---|---|---|---|
| C4 4-(2'-mercaptoethyl)-pyridine | 36.2 | 95.4 | 21.4 |
| 4 4-(2'-tert-butylthioethyl)pyridine | 38.3 | 95.5 | 21.8 |
| 5 4-(2'-thioacetate ethyl)-pyridine | 36.8 | 95.2 | 22.2 |
| 6 2-(2'-tert-butylthioethyl)pyridine | 33.4 | 95.0 | 20.4 |

From the results presented in Tables 1–2, it is evident that the catalysts prepared by the method of the present disclosure using the promoters listed in Tables 1–2, can effectively catalyze the formation of BPA from phenol and acetone. For comparison, when Rohm and Haas A131 resin beads are used under similar conditions as described above, but without an attached promoter, the p,p-BPA produced amounts to about 9.9 wt %, with a pp selectivity of about 83.8%, and a pp/op ratio of about 7.5. Furthermore, when Rohm and Haas A131 resin beads are used under similar conditions as described above, except with a tert-butoxy carbonyl sulfur protected cysteamine promoter, the p,p-BPA produced amounts to about 19.2 wt %, with a pp selectivity of about 93.9%, and a pp/op ratio of about 24.3.

While the invention has been illustrated and described, it is not intended to be limited to the details shown, since various modifications and substitutions can be made without departing in any way from the spirit of the present invention. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A method for forming bisphenols, comprising the step of reacting an aromatic hydroxy compound with a carbonyl containing compound in the presence of a catalyst composition, said catalyst composition comprising a polymeric resin component comprising a protic acid functionality, and a sulfur-protected mercaptan promoter component, wherein said promoter component has the following functionalized pyridine structure (II),

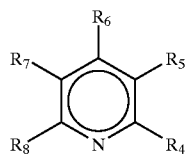

(II)

wherein at least one member selected from the group consisting of $R_4$, $R_5$, $R_6$, $R_7$, and $R_8$ is a $\{(CH_2)_b-S-R_3\}$ chain wherein b is between about 1 and about 11 and $R_3$ is a sulfur-protecting functionality which is one member selected from the group consisting of an aliphatic functionality comprising at least about 4 carbon atoms, an ester functionality comprising between about 1 and about 11 carbon atoms, a carbonate functionality comprising between about 1 and about 11 carbon atoms, and a benzylic functionality comprising at least about 7 carbon atoms which is attached to the sulfur atom via the benzylic methylene carbon; and each of $R_4$, $R_5$, $R_6$, $R_7$, and $R_8$ that is not a $\{(CH_2)_b-S-R_3\}$ chain is independently one member selected from the group consisting of a hydrogen, a fluoride, a bromide, a chloride, an iodide, a vinyl group, a hydroxide, an alkoxide functionality comprising between about 1 and about 11 carbon atoms, an aryloxide functionality comprising at least about 6 carbon atoms, an aliphatic functionality comprising between about 1 and about 11 carbon atoms, an aromatic functionality comprising at least about 6 carbon atoms, a cycloaliphatic ring comprising at least about 5 carbon atoms, said cycloaliphatic ring being fused to the pyridine ring through an adjacent ring substituent cycloaromatic ring comprising at least about 6 carbon atoms, said cycloaromatic ring being fused to the pyridine ring through an adjacent ring substituent.

2. The method of claim 1, wherein the bisphenol which is being formed is 4,4'-isopropylidenediphenol.

3. The method of claim 1, wherein the aromatic hydroxy compound is phenol.

4. The method of claim 1, wherein the carbonyl containing compound is a ketone or an aldehyde.

5. The method of claim 4, wherein the ketone is acetone.

6. The method of claim 1, wherein said polymeric resin comprises at least one member selected from the group consisting of polystyrene, a zeolite, and silica.

7. The method of claim 6, wherein said polymeric resin further comprises divinylbenzene.

8. The method of claim 1, wherein b is 2, and $R_4$ is the $\{(CH_2)_b-S-R_3\}$ chain.

9. The method of claim 1, wherein b is 2, and $R_5$ is the $\{(CH_2)_b-S-R_3\}$ chain.

10. The method of claim 1, wherein b is 2, and $R_6$ is the $\{(CH_2)_b-S-R_3\}$ chain.

11. The method of claim 1, wherein the bisphenol is 4,4'-isopropylidenediphenol, the aromatic hydroxy compound is phenol, the carbonyl containing compound is acetone, and said promoter component is,

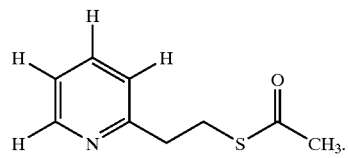

12. The method of claim 1, wherein the bisphenol is 4,4'-isopropylidenediphenol, the aromatic hydroxy compound is phenol, the carbonyl containing compound is acetone, and said promoter component is,

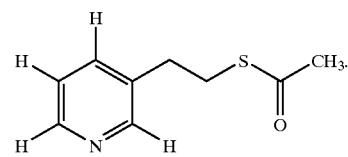

13. The method of claim 1, wherein the bisphenol is 4,4'-isopropylidenediphenol, the aromatic hydroxy compound is phenol, the carbonyl containing compound is acetone, and said promoter component is,

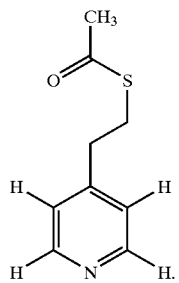

14. The method of claim 1, wherein the bisphenol is 4,4'-isopropylidenediphenol, the aromatic hydroxy compound is phenol, the carbonyl containing compound is acetone, and said promoter component is,

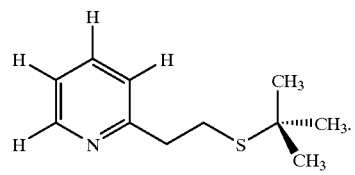

15. The method of claim wherein the bisphenol is 4,4'-isopropylidenediphenol, the aromatic hydroxy compound is phenol, the carbonyl containing compound is acetone, and said promoter component is,

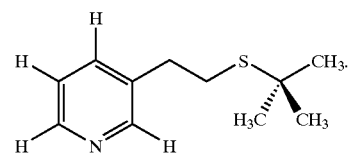

16. The method of claim wherein the bisphenol is 4,4'-isopropylidenediphenol, the aromatic hydroxy compound is phenol, the carbonyl containing compound is acetone, and said promoter component is,

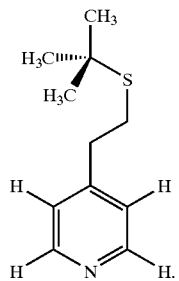

* * * * *